(12) United States Patent
Koch et al.

(10) Patent No.: US 10,098,990 B2
(45) Date of Patent: Oct. 16, 2018

(54) DRAINAGE CONTAINER DEVICE AND SUCTION BAG UNIT

(71) Applicant: MEDELA HOLDING AG, Baar (CH)

(72) Inventors: Urs Koch, Greppen (CH); Hilmar Ehlert, Hergiswil (CH)

(73) Assignee: MEDELA HOLDING AG, Baar (CH)

( * ) Notice: Subject to any disclaimer, the term of this patent is extended or adjusted under 35 U.S.C. 154(b) by 527 days.

(21) Appl. No.: 14/404,157

(22) PCT Filed: May 23, 2013

(86) PCT No.: PCT/CH2013/000089
§ 371 (c)(1),
(2) Date: Nov. 26, 2014

(87) PCT Pub. No.: WO2013/177716
PCT Pub. Date: Dec. 5, 2013

(65) Prior Publication Data
US 2015/0141943 A1 May 21, 2015

(30) Foreign Application Priority Data

May 29, 2012 (CH) ...................................... 0738/12

(51) Int. Cl.
*A61M 1/00* (2006.01)
(52) U.S. Cl.
CPC ........ *A61M 1/0049* (2013.01); *A61M 1/0001* (2013.01); *A61M 1/005* (2014.02);
(Continued)
(58) Field of Classification Search
CPC .. A61M 1/0049; A61M 1/0017; A61M 1/005; A61M 1/0052; A61M 1/0001; A61M 2209/082
See application file for complete search history.

(56) References Cited

U.S. PATENT DOCUMENTS 3,768,478 A     10/1973   Fertik et al.
3,845,765 A * 11/1974   Ikeda .................. A61M 1/0017
                                                                 604/319
(Continued)

FOREIGN PATENT DOCUMENTS

EP     0861668 A1   9/1998
EP     0882440 A2   12/1998
(Continued)

OTHER PUBLICATIONS

International Search Report for Application No. PCT/CH2013/000089, dated Aug. 21, 2013.
(Continued)

*Primary Examiner* — Tatyana Zalukaeva
*Assistant Examiner* — Gabriella Burnette
(74) *Attorney, Agent, or Firm* — Marshall, Gerstein & Borun LLP

(57) ABSTRACT

A drainage container device for collecting suctioned bodily fluids by means of a vacuum source includes a drainage container with a suction port to be connected with the vacuum source; an essentially one-piece container lid for closing and opening the drainage container, and with a drainage port to be connected with a patient drainage line; a suction bag for holding the suctioned bodily fluid, which is arranged on the container lid and accommodated by the drainage container; a channel that runs at least partially through the container lid, which joins an interior space of the suction bag with the suction port by way of an interior space of the drainage container, and is otherwise closed, and a protective element, in particular a filter, for avoiding overflow and/or contamination of the vacuum source by a suctioned bodily fluid.

16 Claims, 6 Drawing Sheets

(52) U.S. Cl.
CPC ........ *A61M 1/0017* (2014.02); *A61M 1/0052* (2014.02); *A61M 2209/082* (2013.01)

(56) References Cited

U.S. PATENT DOCUMENTS

| | | | |
|---|---|---|---|
| 4,111,204 A * | 9/1978 | Hessel | A61M 1/0001 604/321 |
| 4,275,732 A | 6/1981 | Gereg | |
| 4,460,361 A | 7/1984 | Nichols | |
| 4,487,606 A | 12/1984 | Leviton et al. | |
| 6,056,731 A * | 5/2000 | Koetke | A61M 1/0017 604/317 |
| 6,261,276 B1 | 7/2001 | Reitsma | |

FOREIGN PATENT DOCUMENTS

| | | | | |
|---|---|---|---|---|
| EP | 1225930 A1 | 7/2002 | | |
| WO | WO-9414045 A1 | 6/1994 | | |
| WO | WO 0124846 A1 * | 4/2001 | .......... | A61M 1/0001 |
| WO | WO-0124846 A1 | 4/2001 | | |
| WO | WO-2008/144951 A1 | 12/2008 | | |
| WO | WO 2008144951 A1 * | 12/2008 | .......... | A61M 1/0001 |

OTHER PUBLICATIONS

Written Opinion for International Application No. PCT/CH2013/000089, dated Aug. 21, 2013.

* cited by examiner

DRAINAGE CONTAINER DEVICE AND SUCTION BAG UNIT

CROSS-REFERENCE TO RELATED APPLICATION

The present application is the US national phase of International Patent Application No. PCT/CH2013/000089, filed May 23, 2014, which application claims priority to Switzerland Application No. 0738/12, filed May 29, 2012. The priority application, CH 0738/12, is hereby incorporated by reference.

FIELD OF THE DISCLOSURE

The present invention relates to a drainage container device and to a suction bag unit.

PRIOR ART

In the medical area, bodily fluids are suctioned by means of a vacuum source and collected in a drainage container device. Examples for this are surgical procedures, wound drainage, thoracic drainage and suctioning of body fats.

Known in the art are drainage container devices that comprise a rigid drainage container and a lid that tightly seals the latter, with a flexible suction bag secured to the lid. Present inside the lid is a patient drainage port to be connected with a drainage tube leading to the patient. Further present is a suction port, which connects the drainage container device with a suction source, and which generates a vacuum in a cavity of the patient to be suctioned by evacuating the suction bag. The suction port can be arranged in the lid, and directly connected with the suction bag. It can also be arranged in the rigid drainage container, so that first the drainage container and only then the suction bag situated therein are evacuated. To this end, a connecting channel can be provided in the lid between the container interior and the bag interior.

If a suction bag is full, the drainage port is disconnected first, and then the suction port in the lid, if present. The lid along with the suction bag is then removed from the container and disposed. After the container is cleaned in accordance with hospital guidelines, the container can continue to be used for the same patient. If the suction port is arranged in the container, it must not be removed. Suction ports in the lid are disadvantageous, because both the drainage tube connection and the connection to the vacuum source must be disengaged when changing out the bag respectively when emptying out the container. This is time-consuming on the one hand, while there is a danger that the tubes will subsequently be hooked up with the wrong connections on the other hand.

EP 1 225 930 discloses a drainage container device with a one-piece lid and a channel that runs within the lid, which leads to the suction port in the rigid container. A filter for protecting the vacuum source is arranged on the underside of the lid facing the interior of the bag, wherein the filter is adjusted to the end of the channel. The filter used here comprises a u-shaped cross section, and is correspondingly complicated and expensive to manufacture.

WO 94/14045 also describes such a drainage container device, wherein a flat filter is arranged in a multipart lid. This multipart lid entails a high outlay to manufacture and assemble.

U.S. Pat. No. 3,768,478 shows a drainage container device with a suction port in the lid and a channel leading to the container interior. Present underneath the suction port is a hollow space for accommodating a porous pad, which swells upon contact with water, and in conjunction with a watertight and airtight pad lying over it serves as an overflow valve.

U.S. Pat. No. 4,111,204 shows a drainage container device with a suction port in the lid. Below the suction port, the lid comprises a chamber, in which an air permeable and watertight filter is placed. The suction port forms an upper cover for this chamber.

U.S. Pat. No. 4,487,606 also shows a drainage container device with a suction port in the lid, wherein a filter is here secured to the underside of the lid, and covered with a protective cap.

In U.S. Pat. No. 4,460,361, an overflow valve is situated on the underside of the lid in a protruding housing.

The disadvantage to filters situated inside the suction bag is that they are subjected to splashes of suctioned bodily fluids, as a result of which they become clogged relatively quickly. This reduces the suction power. Filters arranged in a chamber are appropriately protected.

U.S. Pat. No. 6,261,276 discloses a bagless container with a manual vacuum pump integrated into the lid. A hydrophobic filter is situated on the outside of the lid. A manual vacuum pump is suitable for emergencies, but not for longer term operation.

DESCRIPTION OF THE INVENTION

Therefore, one object of the invention is to create a drainage container device and a suction bag unit of the kind mentioned at the outset that enables a cost-effective and easy to assemble protective element to avoid overflow and/or contamination of the vacuum source.

The drainage container device for collecting suctioned bodily fluids, in particular bodily liquids, by means of an external vacuum source comprises:

a drainage container with a suction port to be connected with the vacuum source;

an essentially one-piece container lid for closing and opening the container, and with a drainage port to be connected with a patient drainage line;

a suction bag for holding the suctioned bodily fluid, which is arranged on the container lid and accommodated by the drainage container;

a channel that runs at least partially through the container lid, which joins an interior space of the suction bag with the suction port by way of an interior space of the drainage container, and is otherwise closed, and a protective element for avoiding overflow and/or contamination of the vacuum source by a suctioned bodily fluid.

According to the invention, the protective element is situated in the channel, and the channel incorporates a chamber in which the protective element is arranged.

The suction bag unit for use in such a drainage container device comprises:

an essentially one-piece container lid for closing and opening the drainage container, and with a drainage port to be connected with a patient drainage line;

a suction bag for holding the suctioned bodily fluid, which is arranged on the container lid for accommodation in the drainage container;

a channel that runs through the container lid and joins an interior space of the suction bag with an interior space of the drainage container for connection with the suction port, wherein the channel is otherwise closed, and a protective element for avoiding overflow and/or contamination of the vacuum source by suctioned bodily fluid.

According to the invention, the protective element is situated in the channel, and the channel incorporates a chamber in which the protective element is arranged.

The protective element is preferably an air permeable/watertight and/or antibacterial filter. Several filters with the same or differing characteristics can also be arranged one in back of the other in the suctioning direction. Alternatively or additionally, the protective element can be an overflow valve. For example, a filter material can swell upon contact with a liquid, and thereby seal the opening airtight. The filter material can simultaneously comprise an antibacterial design. In the following, the term "filter" is used for all of these types of protective elements. As a consequence, the protective element is used to prevent the vacuum source from becoming contaminated by suctioned bodily fluid and/or to avoid an overflow of the filled suction bag.

The device according to the invention and the unit according to the invention combine the advantages of suctioning on the container side without a suction port in the lid with the advantages of arranging the filter in a chamber. In particular, a planar and flat filter can be used. In addition, several filters can be easily arranged one over the other in the suctioning direction.

A splashguard is preferably on hand, which safeguards the protective element against bodily fluids in relation to the interior space of the suction bag. A premature clogging of the filter openings is prevented, and optimal suction power is ensured up until reaching the maximum fill level. If the chamber is closed toward the bag interior except for suction openings, the filter material protects it against splashes. Additionally or alternatively, the splashguard can be comprised of splashguard elements moulded to a floor directed toward the interior space of the suction bag. In a preferred embodiment, these splashguard elements are projected toward the interior space of the suction bag, whereby they form a nonlinear connection between the interior space and the chamber. Each suction opening is preferably provided with such a splashguard element. Alternatively or additionally, the splashguard can also be a protective cap attachable to the chamber, which covers the chamber, but is spaced apart from it, so that a flow channel is present between the chamber and the protective cap.

Alternatively or additionally, the splashguard can be obtained by having the drainage port comprise a spout that projects into the interior space of the bag, wherein the spout comprises a wall that is longer in the chamber region than in the opposing region. This deflects any splashes to the side of the bag lying opposite the chamber.

The chamber is preferably a constituent of the container lid designed essentially as a single piece. However, it can also be attached to the container lid, or inserted into a corresponding recess of the lid.

Assembly is facilitated if the chamber can be accessed from the upper side of the container lid, i.e., from the side of the container lid facing away from the bag interior. The manufacturing costs of the container lid and the chamber are optimized. In addition, this arrangement makes it possible to fit the suction bag unit with filters even after the suction bag has been attached to the container lid. The unit can also be retrofitted with additional filters.

The advantage to arranging the filter in a chamber is also that the filter size and the filter shape can be selected as desired. In particular, relatively large filter surfaces can be used, which increases the suction power.

The chamber is preferably tightly sealed with a separate chamber cover from an exterior side of the container lid facing away from the suction bag. These chamber covers can be adhesively bonded, welded, soldered or otherwise tightly connected with the container lid.

The protective element is preferably plate-shaped in design. In particular in its plate-shaped configuration, the protective element is preferably placed in the chamber. In a preferred embodiment, the protective element is held in its position by the contact pressure exerted by the chamber cover, once again preferably in its plate-shaped configuration.

A transverse central axis of the protective element preferably aligns with a transverse central axis of the chamber. As a consequence, the protective element in the chamber is straight and not slanted.

The chamber is preferably spaced apart relative to the midpoint of the container lid. This makes it possible to minimize the length of the channel.

In a preferred embodiment, the interior of the chamber comprises a continuous projection to support the protective element, wherein the projection faces an exterior side of the container lid facing away from the interior space.

Additional embodiments are indicated in the dependent claims.

BRIEF DESCRIPTION OF THE DRAWINGS

Preferred embodiments of the invention will be described in the following based on the drawings, which serve only for explanatory purposes, and are not to be construed as limiting. The drawings show.

DESCRIPTION OF PREFERRED EMBODIMENTS

Figure 1:
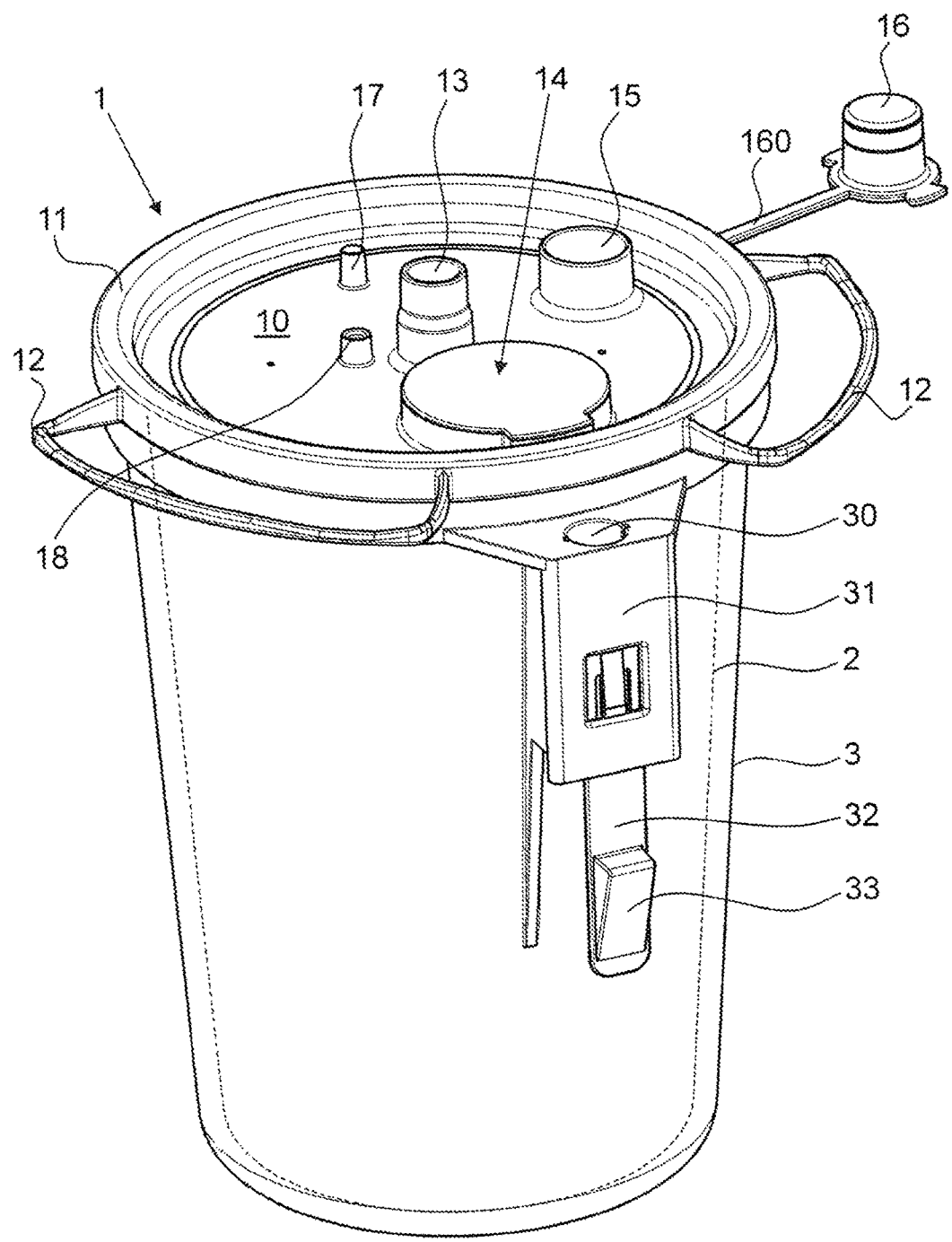
FIG. 1 a perspective view of a drainage container device according to the invention with a drainage container and a container lid.

FIG. 1 shows a preferred embodiment of a drainage container device according to the invention. It encompasses a rigid drainage container 3, which forms an outer container. It preferably consists of a plastic, and in particular is transparent. A container lid 1 is placed on or in the drainage container 3. The container lid 1 seals the drainage container 3 airtight. For this purpose, a sealing ring is preferably present on the drainage container 3 or lid 1.

Figure 8:
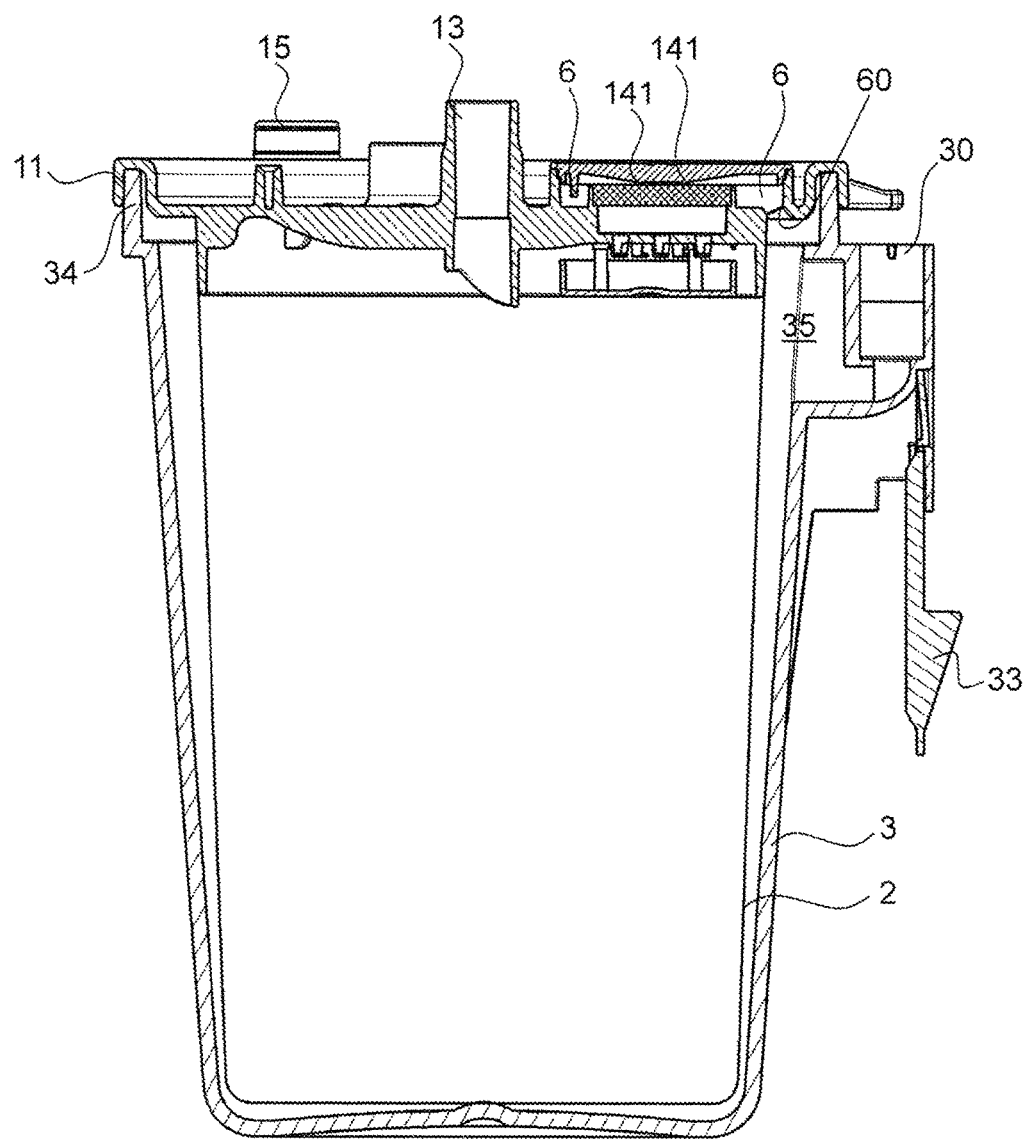
FIG. 8 a longitudinal section through a drainage container device according to the invention in a second embodiment of the invention.

In this example, the edge 11 of the lid 1 comprises a continuous, downwardly open flexible groove 110, which can be pulled over an edge 34 (see FIG. 8) of the container 3.

A flexible suction bag 2 is secured to the lid 1, so that it is incorporated in the container 3 with the lid 1 attached, and can be removed from the container 3 along with the lid 1. The suction bag 2 is preferably adhesively bonded to the lid 1, or welded thereto. At any rate, it is preferably fixedly connected with it. To this end, the lid 1 preferably comprises a continuous apron 19, as may be readily discerned on FIG. 2. The suction bag 2 is preferably attached to an outer or inner surface of this apron 19.

Situated on the container 3 is a vacuum port, here referred to as a suction port 30, to be connected with an external vacuum source (not shown). The suction port 30 is preferably designed as a single piece in conjunction with the remaining container 1. In the exemplary embodiment depicted here, it is located in an attachment projection 31, which protrudes in front of the wall of the container 3, and which is used for securing the container 3 to a rail. For purposes of attachment and simple detachability, this attachment projection 31 preferably comprises a spring element 32 with a retaining nib 33.

For example, the external vacuum source can be a mobile vacuum pump or a central vacuum system of a hospital. The suction port is preferably an opening into which, or a projecting union onto which, a tube leading to the vacuum source can be plugged.

The lid 1 is preferably designed essentially as a single piece. At least the base body 10 is designed as a single piece. For example, individual small parts along with any sealing elements can be formed separately. The lid 1 preferably consists of plastic. It comprises a suitable shape for opening the container 3. It here has a round design.

A drainage port 13 to be connected with a drainage tube leading to a patient is present in the lid 1, more precisely in the base body 10. This drainage port 13 can also be an opening. However, it is preferably a union that outwardly projects from the lid 1, i.e., faces away from the suction bag 2. In this embodiment, the drainage port 13 is centrally arranged in the round lid 1. However, it can also be present at another location.

As illustrated by this embodiment, the lid 1 can additionally comprise a serial port 15 to connect this drainage container device with a second, similarly or identically configured drainage container device. This port is needed when suctioning takes place via two or more containers in series. If only one device is used, this serial port 15 is sealed with a cover lid 16. This cover lid 16 is preferably moulded onto the lid 1 as a single piece. The corresponding connection bracket is marked with reference number 160 on FIG. 1.

The lid 1 preferably comprises handholds 12, so that the lid 1 with the suction bag 2 can be easily removed from the container 3. The handholds 12 are preferably also jointly designed as a single piece with the base body of the lid 1.

As depicted here, fastening unions 17, 18 can be moulded to or on the lid 1, so as to secure additional parts. For example, these fastening unions 17, 18 can serve to attach cover lids for the drainage port 13 and an adapter port for the drainage tube.

Figure 5:
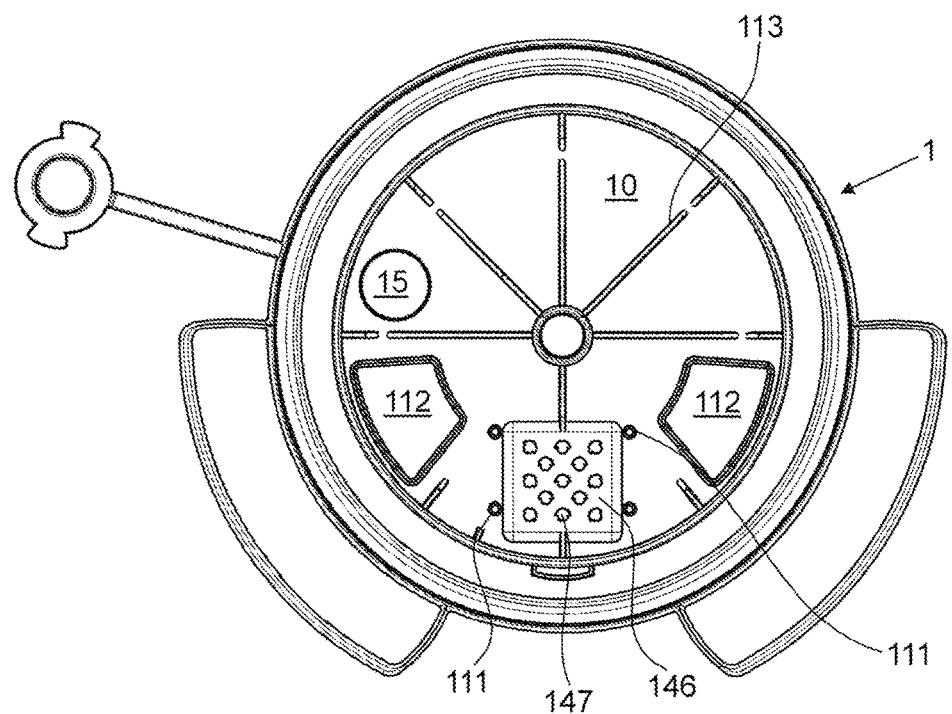
FIG. 5 a view of the container lid according to FIG. 3 from below.
Figure 6:
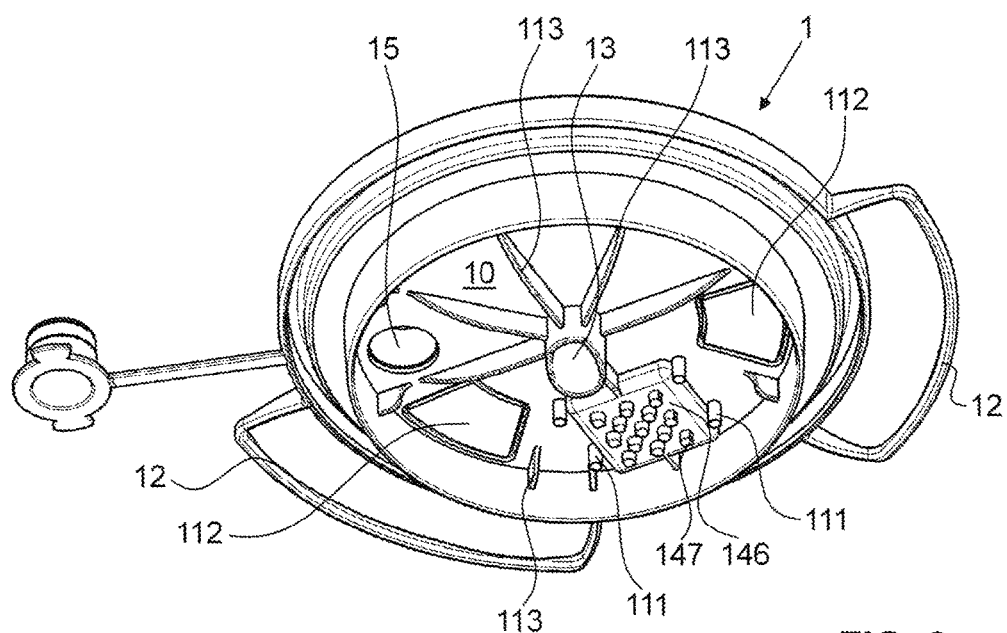
FIG. 6 a perspective view of the container lid according to FIG. 5 from below.
Figure 7:
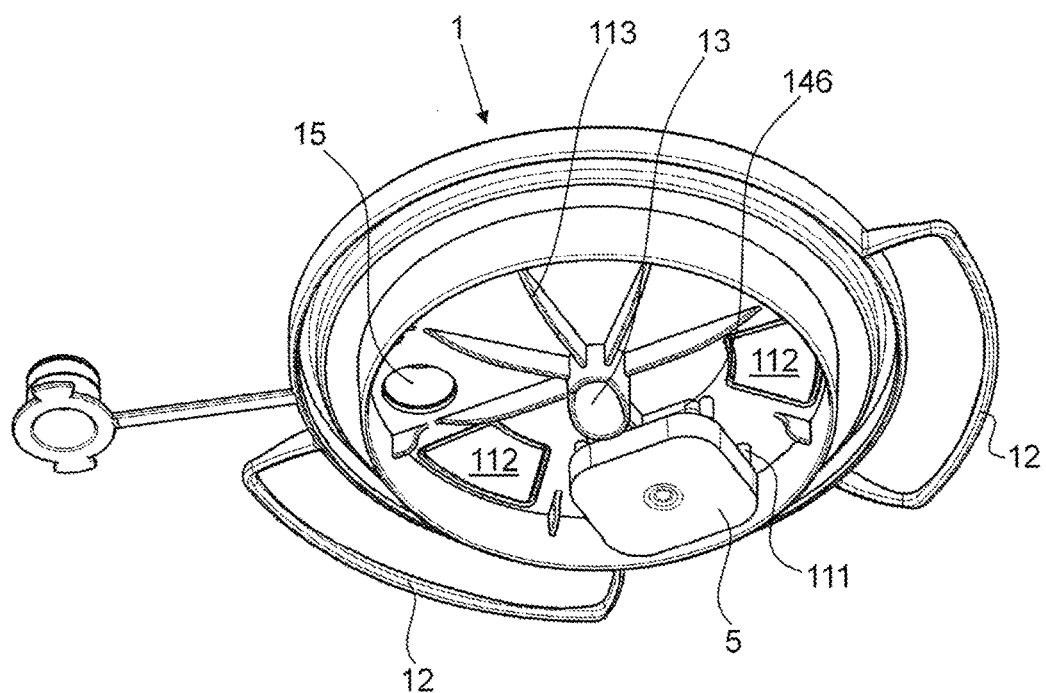
FIG. 7 the container lid according to FIG. 6 with protective cap.

FIGS. 5 to 7 show evacuation windows 112, which are optionally present in the lid 1. They are designed as knock-out parts in the base body 10, and serve to generate openings when the suction bag 2 is full. These windows 112 can be knocked out at a later point, making it possible to evacuate the suction bag 2 after it has been removed from the container 3, and subsequently dispose of the empty suction bag 2. However, the suction bag and the lid can also be disposed of together with the suctioned contents.

Also discernible on FIGS. 5 to 7 are ribs 113, which are optional, and serve to reinforce the lid 1.

Also situated in the lid 1 is a chamber 14, which serves to accommodate a protective element, in particular a filter 4. This is readily discernible from FIG. 2. The chamber 14 is preferably designed as a single piece in conjunction with the base body of the lid 1. It comprises a holding fixture that is open to the top, i.e., faces away from the suction bag 2. This holding fixture is enveloped by an outer wall 142. Located inside this holding fixture is an inner wall 143, which comprises a continuous projection 144. This projection 144 forms a ledge for accommodating the plate-shaped filter 4. This is readily discernible from FIG. 3. The chamber 14 is preferably spaced apart relative to the midpoint of the container lid 1.

The chamber 14 can be designed to be open toward the suction bag 2. However, it preferably comprises a floor 146 that is directed toward the suction bag 2 and incorporates suction openings 148. Otherwise, the floor 146 preferably has a closed design. The suction openings 148 connect the interior space of the bag 2 with the chamber 14. As depicted here, a hollow space 145 can be present between the filter 4 and the floor 146. However, the filter 4 can also rest upon the floor 146, or at least extend up to the floor.

The surface of the protective element is preferably arranged perpendicular to the direction of the flow. In other words, it comprises a transverse central axis that aligns with a transverse central axis of the chamber 14.

Instead of one single filter 4, two or more filters can also be situated one over the other in the chamber 14. The filters 4 can be identical and have the same effect, or comprise different functions. For example, the filter 4 can be antibacterial and/or hydrophobic and/or swell and form an airtight seal when it comes into contact with water. However, the filter 4 can also be a protective filter against smoke. The filters are permeable to air so as to enable suctioning through the filters. If the filter is an overflow valve, i.e., swells, it blocks any continued passage of air in the closed state. The filter can consist of known materials, for example a plastic, in particular a porous polyethylene with swelling properties.

The chamber 14 is sealed with a chamber cover 140. The latter can be applied to the chamber 14 from the outside of the lid 1. The chamber cover 140 is preferably welded, soldered, adhesively bonded or otherwise joined airtight with the outer wall 142 of the chamber 14. As may be gleaned from FIG. 3, the chamber cover 140 preferably comprises a fixing element 141, with which the filter 4 is fixed in its position in the chamber 14. Fixation preferably takes place in an area or at points, preferably at a few points, so as to maximize the surface of the filter 4 through which air can flow.

Figure 3:
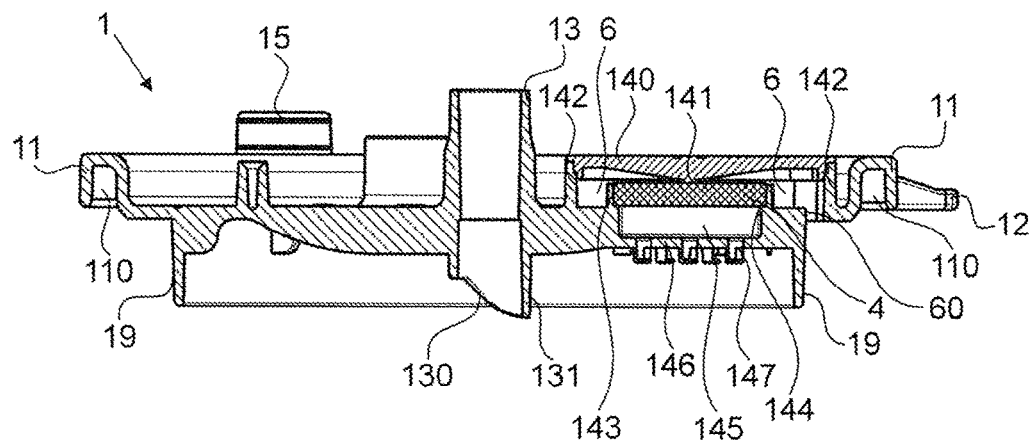
FIG. 3 a longitudinal section through a container lid of the suction bag unit according to FIG. 2, without protective cap.

Visible on FIG. 3 is a channel 6, which runs from the interior space of the suction bag 2 through the lid 1 to the drainage container 3. It here runs through the suction openings 148 in the floor 146 of the chamber 14, through the hollow space 145, through the filter 4 into the gap between the outer and the inner wall 142, 143, until arriving at a container-side end 60. This end 60 empties into the drainage container 3, and establishes a connection to the suction port 30 via the hollow space 35 (see FIG. 8). The channel 6 has a closed design except for the suction openings 148 and the container-side end 60. In particular, it has no additional output opening leading out of the lid 1, i.e., there is no suction port in the lid.

A vacuum applied by the vacuum source in the interior space between the suction bag 2 and the outer wall of the container 3 can now be transferred by way of this channel 6 to the interior space of the suction bag 2, and from there by way of the drainage port 13 and the drainage line to a cavity of the patient to be suctioned. In this way, bodily fluids can be suctioned from the patient into the suction bag 2.

In order to prevent the filter 4 from becoming prematurely clogged, at least one splashguard is preferably on hand. The splashguard is preferably characterized by one or more of the features listed below:

The drainage port 13 preferably comprises a spout that projects into interior space of the suction bag 2, and whose end 130 facing the bag is slanted. The spout is here elongated on the side facing the filter 4. The elongated side part is marked with reference number 131 on FIG. 3.

The suction openings 148 in the essentially closed floor 146 of the chamber 14, in particular in combination with the recessed filter 4, also already comprises a splashguard.

Several, preferably each, of the suction openings are provided with a splashguard element 147 that extends into the interior space of the suction bag 2. These are small caps that are molded to the floor 146 as a single piece, and create a nonlinear access, preferably a right-angled access, from the suction bag 2 into the chamber 14. These splashguard elements 147 are readily discernible on FIGS. 3, 5 and 6.

Figure 2:
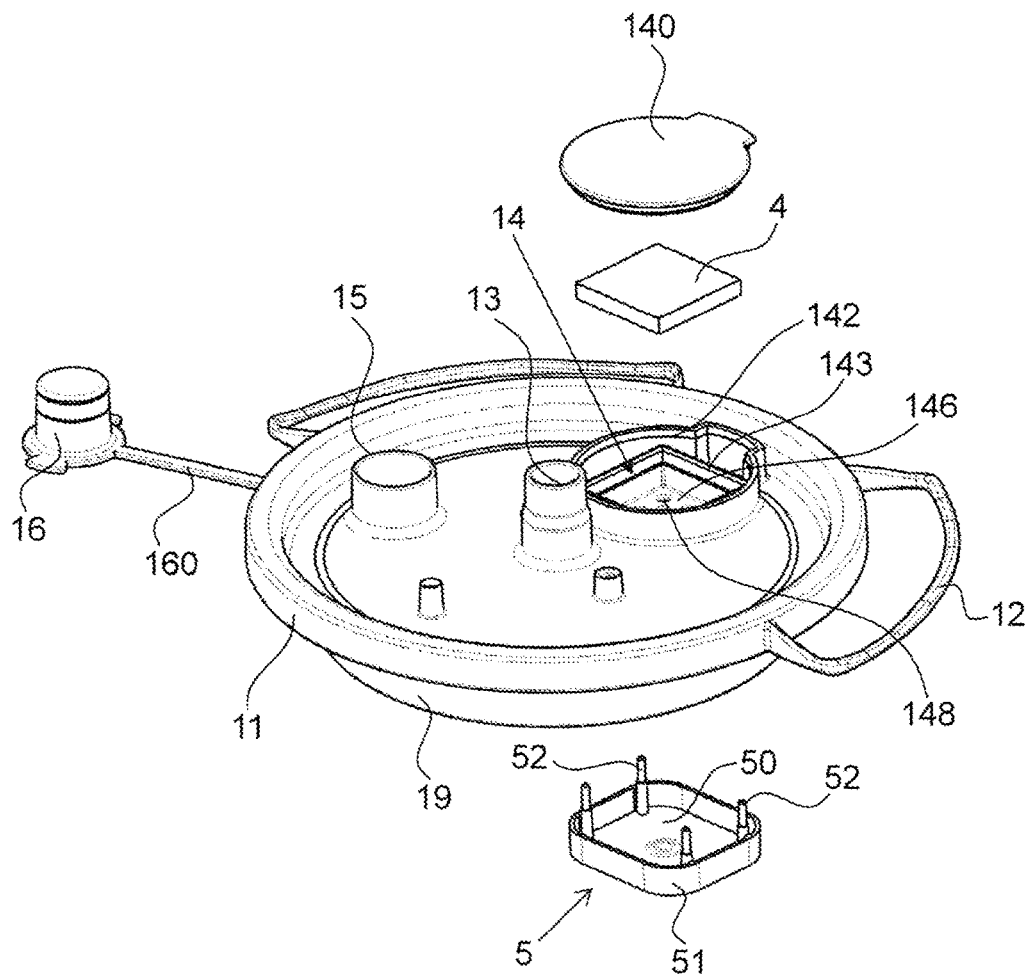
FIG. 2 a perspective view of a suction bag unit according to the invention for exemplary use in the drainage container device according to FIG. 1.
Figure 4:
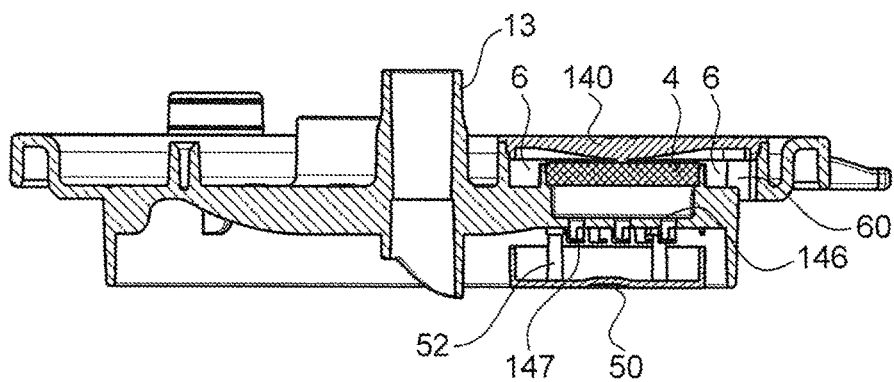
FIG. 4 a longitudinal section through the container lid of the suction bag unit according to FIG. 2, with protective cap.

In the embodiment depicted on FIGS. 2, 4 and 7, the floor 146 of the chamber is additionally covered by a protective cap 5, which projects into the interior space of the suction bag 2. The protective cap 5 is spaced apart from the floor 146, so that air can be aspirated into the chamber through the arising gap. The protective cap 5 preferably comprises a planar floor 50 and a jacket 51 designed perpendicular thereto that rotates completely around the floor 50. Fastening pins 52 are present for attaching the protective cap 5, and can be inserted into corresponding holding fixtures 111 in the container lid 1. The holding fixtures 111 may be gleaned from FIG. 5.

The parts described above are again shown on FIG. 8 in the form of an overview. The embodiment according to FIG. 8 differs from the preceding ones only in that the chamber cover 140 comprises not just one point 141, but rather two or more. These are marked with reference number 141 on the figure. A ring 141 can also be present, which fixes the filter 4 in place.

The device according to the invention and the unit according to the invention enable the easy assembly of a cost-effective filter, wherein they additionally offer a splashguard in preferred embodiments.

What is claimed is:

1. A drainage container device for collecting suctioned bodily fluids by means of a vacuum source, wherein the drainage container device comprises:
   a drainage container with an outer wall and with a suction port to be connected with the vacuum source;
   a container lid for closing and opening the drainage container, having a drainage port to be connected with a patient drainage line;
   a suction bag for holding the suctioned bodily fluid, which is arranged on the container lid and accommodated by the drainage container;
   a channel which runs at least partially through the container lid, which joins an interior space of the suction bag with the suction port by way of an interior space of the drainage container, and which channel is otherwise closed, and
   a protective element for avoiding at least one of overflow or contamination of the vacuum source by a suctioned bodily fluid,
   wherein
   the suction port is arranged on the outer wall of the drainage container such that a vacuum can be applied by the vacuum source in the interior space of the drainage container between the suction bag and the outer wall of the drainage container;
   wherein
   the protective element is situated in the channel, and the channel incorporates a chamber in which the protective element is arranged;
   and wherein
   the chamber is tightly sealed with a separate chamber cover from an exterior side of the container lid facing away from the suction bag.

2. A suction bag unit for use in a drainage container device, wherein the suction bag unit comprises:
   a container lid for closing and opening the drainage container, and with a drainage port to be connected with a patient drainage line;
   a suction bag for holding the suctioned bodily fluid, which is arranged on the container lid for accommodation in the drainage container;
   a channel which runs through the container lid and joins an interior space of the suction bag with an interior space of the drainage container for connection with a suction port arranged on an outer wall of the drainage container, such that a vacuum can be applied by a vacuum source in the interior space of the drainage container between the suction bag and the outer wall of the drainage container, wherein the channel is otherwise closed, and
   a protective element for avoiding at least one of overflow or contamination of the vacuum source by suctioned bodily fluid,
   wherein
   the protective element is situated in the channel, and the channel incorporates a chamber in which the protective element is arranged;
   and wherein
   the chamber is tightly sealed with a separate chamber cover from an exterior side of the container lid facing away from the suction bag.

3. The suction bag unit according to claim 2, wherein the chamber comprises a floor directed toward the interior space of the suction bag, with suction openings for connecting the interior space of the suction bag with the interior space of the drainage container.

4. The suction bag unit according to claim 2, wherein at least one splashguard is present, which safeguards the protective element against bodily fluids in relation to the interior space of the suction bag.

5. The suction bag unit according to claim 3, wherein at least part of the suction openings are each provided with a splashguard element that projects toward the interior space of the suction bag, wherein each splashguard element forms a nonlinear connection between the interior space and the chamber, and acts as a splashguard.

6. The suction bag unit according to claim 4, wherein the splashguard is formed by a protective cap, which, on the side of the chamber facing the interior space is spaced apart from the chamber, and covers the chamber.

7. The suction bag unit according to claim 2, wherein the container lid has a main part being made in one piece, and wherein the chamber is situated in this main part of the container lid.

8. The suction bag unit according to claim 2, wherein the protective element is inserted into the chamber from this exterior side.

9. The suction bag unit according to claim 2, wherein the protective element is a filter.

10. The suction bag unit according to claim 2, wherein the protective element is planar and flat.

11. The suction bag unit according to claim 2, wherein a transverse central axis of the protective element aligns with a transverse central axis of the chamber.

12. The suction bag unit according to claim 2, wherein the chamber is spaced apart from the midpoint of the container lid.

13. The suction bag unit according to claim 2, wherein the interior of the chamber comprises a continuous projection to support the protective element, wherein the projection faces an exterior side of the container lid facing away from the interior space of the suction bag.

14. The suction bag unit according to claim 2, wherein the drainage port comprises a spout that projects into the interior space of the suction bag, wherein the spout is longer on its side facing the chamber than on its opposite side.

15. The drainage container unit according to claim 1, wherein the container lid is an essentially one-piece container lid.

16. The suction bag unit according to claim 2, wherein the container lid is an essentially one-piece container lid.

\* \* \* \* \*